Figure 4A:
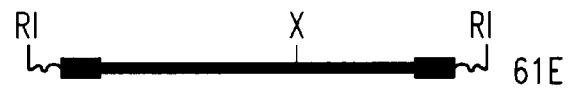

United States Patent [19]

Hoover et al.

[11] Patent Number: 6,042,835
[45] Date of Patent: Mar. 28, 2000

[54] PROTOTYPE FELV ISOLATES FOR USE IN DISEASE MODELS AND VACCINES

[75] Inventors: Edward A. Hoover, Fort Collins, Colo.; James I. Mullins, Brookline, Mass.

[73] Assignees: Colorado State University Research Foundation, Fort Collins, Colo.; Harvard University, Cambridge, Mass.

[21] Appl. No.: 08/233,004

[22] Filed: Apr. 22, 1994

Related U.S. Application Data

[62] Division of application No. 07/939,554, Sep. 1, 1992, abandoned, which is a continuation of application No. 07/284,139, Dec. 13, 1988, abandoned.

[51] Int. Cl.[7] .......................... A61K 39/21; A61K 39/12; A01N 63/00; C12P 21/06
[52] U.S. Cl. .................................. 424/207.1; 424/184.1; 424/204.1; 424/93.6; 424/819; 435/69.1; 435/69.3; 435/320.1; 435/235.1
[58] Field of Search .................................. 435/67.1, 69.3, 435/320.1, 235.41; 424/20.1, 184.1, 204.1, 93.6, 819

[56] References Cited

U.S. PATENT DOCUMENTS

| | | | |
|---|---|---|---|
| 3,966,907 | 6/1976 | Jarrett et al. | 424/89 |
| 4,034,081 | 7/1977 | Jarrett et al. | 424/89 |
| 4,086,134 | 4/1978 | Jarrett et al. | 195/1.2 |
| 4,117,112 | 9/1978 | Jarrett et al. | 424/89 |
| 4,264,587 | 4/1981 | Pedersen et al. | 424/89 |
| 4,332,793 | 6/1982 | Olson | 424/89 |
| 4,405,712 | 9/1983 | Vande Woude et al. | 435/5 |
| 4,406,885 | 9/1983 | Pinter | 424/88 |
| 4,434,157 | 2/1984 | Olsen | 424/89 |
| 4,593,002 | 6/1986 | Dulbecco | 435/172.3 |
| 4,663,436 | 5/1987 | Elder et al. | 530/324 |
| 4,699,785 | 10/1987 | Pedersen | 424/89 |
| 4,701,416 | 10/1987 | Nunberg | 435/320 |
| 4,734,362 | 3/1988 | Hung et al. | 435/68 |
| 4,748,234 | 5/1988 | Dorin et al. | 530/412 |
| 4,789,702 | 12/1988 | Nunberg | 530/324 |
| 4,794,168 | 12/1988 | Elder et al. | 530/324 |
| 4,876,089 | 10/1989 | Lucjw et al. | 424/89 |
| 5,306,493 | 4/1994 | Kelsey | 424/89 |

FOREIGN PATENT DOCUMENTS

| | | | |
|---|---|---|---|
| 0 156 299 | 10/1985 | European Pat. Off. | C12N 15/00 |
| 0 216 564 | 4/1987 | European Pat. Off. | C12N 15/00 |
| 0 260 148 | 3/1988 | European Pat. Off. | C12N 15/00 |
| 0 262 887 | 4/1988 | European Pat. Off. | C12N 5/00 |
| 0 307 248 | 3/1989 | European Pat. Off. | C12N 15/00 |
| 88/05783 | 8/1988 | WIPO | C07K 7/06 |

OTHER PUBLICATIONS

Hoover, Edward A. et al. "Protection against feline leukemia virus infection by use of an inactivated virus vaccine," *JAVMA* 199(10):1392–1401.

Hoover, Edward A. et al. "Experimental Transmission and Pathogenesis of Immunodeficiency Syndrome in Cats," *Blood* 70(6):1880–1892, 1987.

Stewart, Monica A. et al. "Nucleotide Sequences of a Feline Leukemia Virus Subgroup A Envelope Gene and Long Terminal Repeat and Evidence for the Recombinational Origin of Subgroup B Viruses," *Journal of Virology* 58(3):825–834, 1986.

Mullins, James I. et al. "Disease–specific and tissue–specific production of unintegrated feline leukaemia virus variant DNA in feline AIDS," *Nature* 319:333–336, 1986.

Overbaugh, Julie et al. "Molecular Cloning of a Feline Leukemia Virus That Induces Fatal Immunodeficiency Disease in Cats," *Science* 239:906–910, 1988.

Overbaugh, Julie et al. "Transduction of endogenous envelope genes by feline leukemia virus in vitro," *Nature* 332:731–734, 1988.

Donahue, Peter R. "Strong Sequence Conservation among Horizontally Transmissible, Minimally Pathogenic Feline Leukemia Viruses," *Journal of Virology* 62(3):722–731, 1988.

Overbaugh et al. Cold Spring Harbor Laboratory Abstracts of Papers Presented at the 1986 Meeting on RNA Tumor Viruses, May 20–25, 1986, describes variability in feline AIDS virus genomes, p. 141.

Donahue et al. Cold Spring Harbor Laboratory Abstracts of Papers Presented at the 1987 Meeting on RNA Tumor Viruses, May 19–May 24, 1987, describes pathogenic determinants of the feline AIDS virus.

Stewart et al. *J. Virology* 58(3):825–834, 1986, describes nucleotide sequences of a feline leukemia virus subgroup A envelope gene and long terminal repeat.

Smith, Geoffrey et al. "Construction and characterization of an infectious vaccinia virus recombinant that expresses the influenze hemagglutinin gene and induces resistance to influenze virus infection in hamsters," *Proc. Natl. Acad. Sci.* 80:7155–7159, 1983.

Chakrabarti, Sekhar et al. "Vaccinia Virus Expression Vector: Coexpression of β–Galactosidase Provides Visual Screening of Recombinant Virus Plaques," *Molecular and Cellular Biology* 5(12):3403–3409, 1985.

Starcich, Bruno R. et al. "Identification and Characterization of Conserved and Variable Regions in the Envelope Gene of HTLV–III/LAV, the Retrovirus of AIDS," *Cell* 45:637–648, 1986.

(List continued on next page.)

*Primary Examiner*—Frank C. Eisenschenk
*Assistant Examiner*—Mary K Zeman
*Attorney, Agent, or Firm*—Seed and Berry LLP

[57] ABSTRACT

Molecular clones of feline leukemia virus isolates that encode (a) a prototype highly infectious, minimally pathogenic virus, (b) a variant genome that is replication-defective and associated with a fatal immunodeficiency in cats similar to AIDS (FAIDS) or (c) a chimeric genome that is replication-competent and induces FAIDS. These molecular clones may be used to generate cell lines producing infectious virus which is useful in the preparation of vaccines or in the generation of viremia or disease challenge systems.

25 Claims, 11 Drawing Sheets

OTHER PUBLICATIONS

Hahn, Beatrice H. Hahn et al. "Genomic diversity of the acquired immune deficiency syndrome virus HTLV–III: Different viruses exhibit greatest divergence in their envelope genes," *Proc. Natl. Acad. Sci.* 82:4813–4817, 1985.

Devarc, S.G. et al. "Genomic diversity of the acquired immunodeficiency syndrome retroviruses is reflected in alteration of its translational products," *Proc. Natl. Acad. Sci.* 83:5718–5722, 1986.

Montelaro, Ronald C. "Antigenic Variation during Persitent Infection by Equine Infectious Anemia Virus, a Retrovirus," *The Journal of Biological Chemistry* 259(16): 10539–10544, 1984.

Pedersen, N.C. et al. "Possible immunoenhancement of persistent viremia by feline leukemia virus envelope glycoprotein vaccines in challenge–exposure situations where whole inactivated virus vaccines were protective," *Veterinary Immunology and Immunopathology* 11:123–148, 1986.

Riedel et al. "Evolution of Feline Leukemia Viruses," *Cold Spring Harbor Laboratory 1986 Meeting on RNA Tumor Viruses,* May 20–May 25, 1986.

Rübsamen–Waigmann, H. "Isolation of Variants of Lymphocytopathic Retroviruses From the Peripheral Blood and Cerebrospinal Fluid of Patients With ARC or AIDS," *Journal of Medical Virology* 19:335–344, 1986.

Hardy, William D., Jr., et al. "Biology of Feline Leukemia Virus in the Natural Environment," *Cancer Research* 36:582–588, 1976.

Hahn, Beatrice H. et al. "Genetic Variation in HTLV–III/ LAV Over Time in Patients with AIDS or at Risk for AIDS," *Science* 232:1548–1553, 1986.

Sebring et al. *J. Am. Vet. Med. Assoc.* 199:1413–1419.

Legendre et al. *Am. Vet. Med. Assoc.* 199:1456–1462.

Burie et al. Science 247:1306–1310 1990.

Burgess et al. J. Cell Biology 111:2129–38, Nov. 1990.

Cozpr et al. Mol. Cell Biol. 8(3):1247–52, Mar. 1988.

```
                                         ↓PstI.
   1  TGAAAGACCCCCTACCCCAAAATTTAGCCAGCTACTGCAGTGGTGCCATTTCACAAGGCATGGAAAATTAC   70
  71  TCAAGTATGTTCCCATGAGATACAAGGAAGTTAGAGGCTAAAACAGGATATCTGTGGTTAAGCACCTGGG  140
 141  CCCCGGCTTGAGGCCAAGAACAGTTAAACCCCGGATATAGCTGAAACAGCAGAAGTTTCAAGGCCGCTGC  210
 211  CAGCAGTCTCCAGGCTCCCCAGTTGACCAGAGTTCGACCTTCCGCCTCATTTAAACTAACCAATCCCCAT  280
 281  GCCTCTCGCTTCTGRACGCGCGCTTTCTGCTATAAAACGAGCCATCAGCCCCCAACGGGCGCGCAAGTCT  350
                 ↓SmaI
 351  TTGCTGAGACTTGACCGCCCCGGGTACCCGRGRACGAATAAACCTCTTGCCGATTGCATCTGACTCGTGG  420
                              ↑KpnI
 421  TCTCGGTCTTCCGTGGGCGCGGGGCCTCATCGCCGAGGAAGACCCAGTTCGGGGGTCTTTCATTTGGGGG  490
                          ↓SmaI
 491  CTCGTCCGGGATAGAGACCCCCAACCCCCGGGACCACCGACCCACCATCAGGAGGTAAGCTGGCCGGCGA  560
 561  CCATATCTGTTGTCCTTGTATAAGTGTCTCTGTCAATTGATCTGATTTTGGCGGTGGGATCGAAGGAGCT  630
 631  GACGAGCTCGTACTTCGCCCCCGCAACCCTGGAAGACGTTCCACGGGTGTCTGATGTCTGGAGCCTCTAG  700
                                                                 M  S  G  A  S  S
 701  TGGGACAGCCATTGGGGCTCATCTGTTTGGGGTCTCACCTGAATACAGGGTGTTGATCGGAGACGAGGGA  770
       G  T  A  I  G  A  H  L  F  G  V  S  P  E  Y  R  V  L  I  G  D  E  G
                                                       ↓KpnI
 771  GCCGGACCCTCAAAGTCTCTTTCTGAGGTTTCATTTTCGGTTTGGTACCGAAGCCGCGCGGCACGTCTTG  840
       A  G  P  S  K  S  L  S  E  V  S  F  S  V  W  Y  R  S  R  A  A  R  L  V
 841  TCATTTTTTGTCTGGTTGCGTCTTTTCTTGTCCCTTGTCTAACCTTTTTAATTGCAGAAACCGTCATGGG  910
       I  F  C  L  V  A  S  F  L  V  P  C  L  T  F  L  I  A  E  T  V  M  G
 911  CCAAACTATAACTACCCCCTTAAGCCTCACCCTTGATCACTGGTCTGAAGTCCGGGCACGAGCCCATAAT  980
       Q  T  I  T  T  P  L  S  L  T  L  D  H  W  S  E  V  R  A  R  A  H  N
 981  CAAGGTCTCGAGVTCCGGAAAAAGAAATGGATTACCTTATGTGAGGCCGAATGGGTGATGATGAATGTGG 1050
       Q  G  V  E  V  R  K  K  K  W  I  T  L  C  E  A  E  W  V  M  M  N  V  G
                                                             ↓BglII     ↓SmaI.
1051  GCTGGCCCCGAGAAGGAACTTTTTCTCTTGATAACATTTCCCAGGTTGAGAAAAAGATCTTCGCCCCGGG 1120
       W  P  R  E  G  T  F  S  L  D  N  I  S  Q  V  E  K  K  I  F  A  P  G
1121  ACCGTATGGACACCCCGACCAAGTTCCGTACATTACCACATGGAGATCCTTAGCCACAGACCCCCCTTCG 1190
       P  Y  G  H  P  D  Q  V  P  Y  I  T  T  W  R  S  L  A  T  D  P  P  S
1191  TGGGTTCGTCCGTTCCTACCCCCTCCCAAAACTCCCACACCCCTCCCTCAACCTCTATCGCCGCAGCCCT 1260
       W  V  R  P  F  L  P  P  P  K  T  P  T  P  L  P  Q  P  L  S  P  Q  P  S
1261  CCGCCCCTCTTACCTCTTCCCTCTACCCCGTTCTCCCCAAGTCAGACCCTCCCAAACCGCCTGTGTTACC 1330
       A  P  L  T  S  S  L  Y  P  V  L  P  K  S  D  P  P  K  P  P  V  L  P
1331  GCCTGATCCTTCTTCCCCTTTAATTGATCTCTTAACAGAAGAGCCACCTCCCTATCCGGGGGGTCACGGG 1400
       P  D  P  S  S  P  L  I  D  L  L  T  E  E  P  P  P  Y  P  G  G  H  G
```

*Fig. 1A*

```
1401  CCACCGCCATCAGGTCCTAGAACCCCAACCGCTTCCCCGATTGCCAGCCGGCTAAGGGAACGACGAGAAA  1470
       P  P  P  S  G  P  R  T  P  T  A  S  P  I  A  S  R  L  R  E  R  R  E  N

1471  ACCCTGCTGAAGAATCTCAAGCCCTCCCCTTGAGGGAAGGCCCCAACAACCGGCCCCAGTATTGGCCATT  1540
       P  A  E  E  S  Q  A  L  P  L  R  E  G  P  N  N  R  P  Q  Y  W  P  F

1541  CTCAGCTTCAGACCTGTATAACTGGAAGTCGCATAACCCCCCTTTCTCCCAAGACCCCGTGGCCCTAACT  1610
       S  A  S  D  L  Y  N  W  K  S  H  N  P  P  F  S  Q  D  P  V  A  L  T

1611  AACCTAATTGAGTCCATTTTAGTGACGCATCAACCAACCTGGGACGACTGCCAGCAGCTCTTGCAGGCAC  1680
       N  L  I  E  S  I  L  V  T  H  Q  P  T  W  D  D  C  Q  Q  L  L  Q  A  L

1681  TCCTGACAGGCGAAGAAAGGCAAAGGGTCCTTCTTGAGGCCCGAAAGCAGGTTCCAGGCGAGGACGGACG  1750
       L  T  G  E  E  R  Q  R  V  L  L  E  A  R  K  Q  V  P  G  E  D  G  R
                                      ↓HindIII
1751  GCCAACCCAGCTGCCCAATGTCATTGACGAAGCTTTCCCCTTGACCCGTCCCAACTGGGATTTTCGTACG  1820
       P  T  Q  L  P  N  V  I  D  E  A  F  P  L  T  R  P  N  W  D  F  R  T
                                                              ↓SacII.
1821  CCGGCAGGTAGGGAGCACCTACGCCTTTATCGCCAGTTGCTGTTAGCGGGTCTCCGCGGGGCTGCAAGAC  1890
       P  A  G  R  E  H  L  R  L  Y  R  Q  L  L  L  A  G  L  R  G  A  A  R  R 1891  GCCCCACTAATTTGGCACAGGTAAAGCAAGTTGTACAAGGGAAAGAGGAAACGCCAGCCTCATTCTTAGA  1960
       P  T  N  L  A  Q  V  K  Q  V  V  Q  G  K  E  E  T  P  A  S  F  L  E 1961  AAGATTAAAAGAGGCTTACAGAATGTATACTCCCTATGACCCTGAGGACCCAGGGCAGGCTGCTAGTGTT  2030
       R  L  K  E  A  Y  R  M  Y  T  P  Y  D  P  E  D  P  G  Q  A  A  S  V 2031  ATCCTGTCCTTTATCTACCAGTCTAGCCCGGACATAAGAAATAAGTTACAAAGGCTAGAAGGCCTACAGG  2100
       I  L  S  F  I  Y  Q  S  S  P  D  I  R  N  K  L  Q  R  L  E  G  L  Q  G 2101  GGTTCACACTGTCTGATTTGCTAAAAGAGGCAGAAAAGATATACAACAAAAGGGAGACCCCAGAGGAAAG  2170
       F  T  L  S  D  L  L  K  E  A  E  K  I  Y  N  K  R  E  T  P  E  E  R 2171  GGAAGAAAGATTATGGCAGCGGCAGGAAGAAAGAGATAAAAAGCGCCATAAGGAGATGACTAAAGTTCTG  2240
       E  E  R  L  W  Q  R  Q  E  E  R  D  K  K  R  H  K  E  M  T  K  V  L 2241  GCCACAGTAGTTGCTCAGAATAGAGATAAGGATAGAGAGGAAAGTAAACTGGGAGATCAAAGAAAAATAC  2310
       A  T  V  V  A  Q  N  R  D  K  D  R  E  E  S  K  L  G  D  Q  R  K  I  P 2311  CTCTGGGGAAAGACCAGTGTGCCTATTGCAAGGAAAAGGGACATTGGGTTCGCGATTGCCCCAAACGGCC  2380
       L  G  K  D  Q  C  A  Y  C  K  E  K  G  H  W  V  R  D  C  P  K  R  P 2381  CCGGAAGAAACCCGCCAACTCCACTCTCCTCAACTTAGAAGATTAGGAGAGTCAGGGCCAGGACCCCCCC  2450
       R  K  K  P  A  N  S  T  L  L  N  L  E  D  Z  E  S  Q  G  Q  D  P  P 2451  CCTGAGCCCAGGATAACCTTAAAAATAGGGGGGCAACCGGTGACTTTCCTGGTGGACACGGGAGCCCAGC  2520
       P  E  P  R  I  T  L  K  I  G  G  Q  P  V  T  F  L  V  D  T  G  A  Q  H 2521  ACTCAGTATTAACTCGACCAGATGGACCTCTCAGTGACCGCACAGCCCTGGTGCAAGGAGCCACGGGAAG  2590
       S  V  L  T  R  P  D  G  P  L  S  D  R  T  A  L  V  Q  G  A  T  G  S
```

*Fig. 1B*

```
2591  CAAAAACTACCGGTGGACCACCGACAGGAGGGTACAACTGGCAACCGGTAAGGTGACTCATTCTTTTTTA  2660
       K  N  Y  R  W  T  T  D  R  R  V  Q  L  A  T  G  K  V  T  H  S  F  L

2661  TATGTACCTGAATGTCCCTACCCGTTATTAGGAAGAGACCTATTAACTAAACTTAAGGCCCAAATCCATT  2730
       Y  V  P  E  C  P  Y  P  L  L  G  R  D  L  L  T  K  L  K  A  Q  I  H  F

2731  TTACCGGAGAAGGGGCTAATGTTGTTGGGCCCAGGGGTTTACCCCTACAAGTCCTTACTCTACAATTAGA  2800
        T  G  E  G  A  N  V  V  G  P  R  G  L  P  L  Q  V  L  T  L  Q  L  E

2801  AGAAGAGTATCGGCTATTTGAGCCAGAAAGTACACAAAAACAGGAGATGGACATTTGGCTTAAAAACTTT  2870
       E  E  Y  R  L  F  E  P  E  S  T  Q  K  Q  E  M  D  I  W  L  K  N  F

2871  CCCCAGGCATGGGCAGAAAGAGGAGGTATGGGAATGGCTCATTGTCAAGCCCCCGTTCTCATTCAACTTA  2940
       P  Q  A  W  A  E  T  G  G  M  G  M  A  H  C  Q  A  P  V  L  I  Q  L  K

2941  AGGCTACTGCCACTCCAATCTCCATCCGACAGTATCCTATGCCCCATGAAGCCTACCAGGGAATTAAACC  3010
        A  T  A  T  P  I  S  I  R  Q  Y  P  M  P  H  E  A  Y  Q  G  I  K  P

3011  TCATATAAGAAGAATCGTAGATCAAGGCATCCTCAAGCCCTGCCAGTCCCCATGGAATACACCCTTATTA  3080
       H  I  R  R  M  L  D  Q  G  I  L  K  P  C  Q  S  P  W  N  T  P  L  L

3081  CCTGTTAAGAAGCCAGGGACCAAGGATTACAGACCAGTGCAGGACTTAAGAGAAGTAAACAAAAGAGTAG  3150
       P  V  K  K  P  G  T  K  D  Y  R  P  V  Q  D  L  R  E  V  N  K  R  V  E

3151  AAGACATCCATCCTACTGTGCCAAATCCATATAACCTCCTTAGCACCCTCCCGCCGTCTCACCCTTGGTA  3220
        D  I  H  P  T  V  P  N  P  Y  N  L  L  S  T  L  P  P  S  H  P  W  Y

3221  CACTGTCCTAGATTTAAAAGACGCTTTTTTCTGCCTGCGACTACACTCTGAGAGTCAATTACTTTTTGCA  3290
       T  V  L  D  L  K  D  A  F  F  C  L  R  L  H  S  E  S  Q  L  L  F  A

3291  TTTGAATGGAGAGATCCAGAAATAGGACTGTCAGGGCAGCTAACCTGGACACGCCTTCCTCAGGGGTTCA  3360
       F  E  W  R  D  P  E  I  G  L  S  G  Q  L  T  W  T  R  L  P  Q  G  F  K
                                                                    ↓KpnI
3361  AGAACAGCCCCACCCTATTTGATGAGGCTCTGCACTCAGACCTGGCCGATTTCAGGGTAAGGTACCCGGC  3430
       N  S  P  T  L  F  D  E  A  L  H  S  D  L  A  D  F  R  V  R  Y  P  A

3431  TCTAGTCCTCCTACAATATGTAGATGACCTCTTGCTGGCTGCGGCAACCAGGACTGAATGCCTGGAAGGG  3500
       L  V  L  L  Q  Y  V  D  D  L  L  L  A  A  A  T  R  T  E  C  L  E  G
                                     ↓KpnI
3501  ACTAAGGCACTCCTTGAGACTTTGGGCAATAAGGGGTACCGAGCCTCTGCAAAGAAGGCCCAAATTTGCC  3570
       T  K  A  L  L  E  T  L  G  N  K  G  Y  R  A  S  A  K  K  A  Q  I  C  L

3571  TGCAAGAAGTCACATACCTGGGGTACTCTTTAAAAGATGGCCAAAGGTGGCTTACCAAAGCTCGCAAAGA  3640
        Q  E  V  T  Y  L  G  Y  S  L  K  D  G  Q  R  W  L  T  K  A  R  K  E
                                                                   ↓PstI
3641  AGCCATCCTATCCATCCCTGTGCCTAAAAACCCACGACAAGTAAGAGAGTTCCTTGGAACTGCAGGTTAC  3710
       A  I  L  S  I  P  V  P  K  N  P  R  Q  V  R  E  F  L  G  T  A  G  Y

3711  TGCCGGCTGTGGATTCCCGGTTTTGCCGAGCTCGCAGCCCCGCTATACCCTCTCACTCGACCAGGAACTC  3780
       C  R  L  W  I  P  G  F  A  E  L  A  A  P  L  Y  P  L  T  R  P  G  T  L
```

*Fig. 1C*

```
3781  TGTTCCAGTGGGGAACAGAGCAACAATTGGCCTTCGAGAACATTAGAAAGGCCCTCTTGAGTTCCCCTGC  3850
       F  Q  W  G  T  E  Q  Q  L  A  F  E  N  I  R  K  A  L  L  S  S  P  A
3851  CCTGGGGTTGCCAGATATCACCAAGCCCTTTGAATTATTTATTGATGAGAACTCAGGATTTGCGAAGGGG  3920
       L  G  L  P  D  I  T  K  P  F  E  L  F  I  D  E  N  S  G  F  A  K  G

3921  GTGTTAGTCCAAAAACTGGGACCCTGGAAAAGACCAGTTGCCTACCTATCAAAAAAGCTGGATACAGTGG  3990
       V  L  V  Q  K  L  G  P  W  K  R  P  V  A  Y  L  S  K  K  L  D  T  V  A
3991  CATCTGGATGGCCCCCTTGTTTACGCATGGTTGCAGCCATCGCCATCCTAGTCAAGGATGCAGGGAAGCT  4060
       S  G  W  P  P  C  L  R  M  V  A  A  I  A  I  L  V  K  D  A  G  K  L
4061  AACCCTAGGACAGCCGCTAACTATCCTGACCTCCCACCCAGTTGAGGCACTTGTCCGACAGCCTCCAAAT  4130
       T  L  G  Q  P  L  T  I  L  T  S  H  P  V  E  A  L  V  R  Q  P  P  N
4131  AAATGGCTCTCTAATGCTAGAATGACTCATTACCAAGCTATGCTCCTCGATGCAGAGCGAGTCCATTTCG  4200
       K  W  L  S  N  A  R  M  T  H  Y  Q  A  M  L  L  D  A  E  R  V  H  F  G
4201  GGCCGACAGTCTCCCTTAACCCTGCTACTTTGCTCCCCCTCCCCAGCGGGAAACCACCACGACTGTCTCC  4270
       P  T  V  S  L  N  P  A  T  L  L  P  L  P  S  G  K  P  P  R  L  S  P
4271  AGATTTAGCCGAGACCATGGCACAGACCGACTTAACTGACCAGCCGTTGCCGGATGCAGACCTGACCTGG  4340
       D  L  A  E  T  M  A  Q  T  D  L  T  D  Q  P  L  P  D  A  D  L  T  W
4341  TACACGGATGGTAGCAGCTTCATCCGTAACGGAGAGAGAAAAGCCGGAGCCGCAGTAACAACCGAATCTG  4410
       Y  T  D  G  S  S  F  I  R  N  G  E  R  K  A  G  A  A  V  T  T  E  S  E
4411  AGGTAATCTGGGCTGCTTCCCTCCCACCCGGAACGTCAGCCCAGCGAGCCGAACTGATTGCCCTGACCCA  4480
       V  I  W  A  A  S  L  P  P  G  T  S  A  Q  R  A  E  L  I  A  L  T  Q
4481  GGCACTGAAGATGGCAAAAGGTAAGAAGCTAACTGTCTATACGGACAGCCGATATGCCTTTGCTACAGCT  4550
       A  L  K  M  A  K  G  K  K  L  T  V  Y  T  D  S  R  Y  A  F  A  T  A
4551  CATGTACACGGGGAAATCTACAGGCGGCGGGGCCTGCTAACTTCAGAAGGAAAAGAAATTAAAAATAAAA  4620
       H  V  H  G  E  I  Y  R  R  R  G  L  L  T  S  E  G  K  E  I  K  N  K  N
                                                                    ↓SmaI
4621  ATGAAATCCTCGCCCTATTAGAGGCGTTATTCTTACCCAAAAGACTGAGTATCATCCATTGCCCGGGACA  4690
       E  I  L  A  L  L  E  A  L  F  L  P  K  R  L  S  I  I  H  C  P  G  H
4691  CCAAAAAGGCGATAGTCCCCAGGCGAAAGGAAACAGATTAGCCGATGATACAGCAAAGAAAGCCGCCACA  4760
       Q  K  G  D  S  P  Q  A  K  G  N  R  L  A  D  D  T  A  K  K  A  A  T
4761  GAGACTCAATCATCACTAACCATCTTACCCACTGAACTTATAGAGGGTCCCAAAAGGCCTCCATGGGAAT  4830
       E  T  Q  S  S  L  T  I  L  P  T  E  L  I  E  G  P  K  R  P  P  W  E  Y
                                                                    ↓KpnI
4831  ATGATGACAGTGATTTAGACCTTGTGCAGAAACTCGAAGCTCATTATGAGCCAAAAAGAGGGTACCTGGGA  4900
       D  D  S  D  L  D  L  V  Q  K  L  E  A  H  Y  E  P  K  R  G  T  W  E
4901  GTACCGAGGGAAAACTATAATGCCTGAAAAATACGCAAAGGAGTTGATTAGCCATCTGCATAAGTTAACA  4970
       Y  R  G  K  T  I  M  P  E  K  Y  A  K  E  L  I  S  H  L  H  K  L  T
```

*Fig. 1D*

```
4971 CACCTCAGTGCTAGAAAAATGAAAACTTTACTAGAAAGAGAAGAAACTGGGTTTTACCTCCCTAACAGAG 5040
      H  L  S  A  R  K  M  K  T  L  L  E  R  E  E  T  G  F  Y  L  P  N  R  D

5041 ACTTACACCTCCGGCAAGTAACAGAGAGCTGCCGGGCATGTGCTCAAATCAACGCAGGAAAGATAAAGTT 5110
       L  H  L  R  Q  V  T  E  S  C  R  A  C  A  Q  I  N  A  G  K  I  K  F

5111 TGGACCTGATGTAAGGGCCCGAGGCCGCCGGCCCGGAACACATTGGGAAGTAGACTTCACTGAAATCAAG 5180
      G  P  D  V  R  A  R  G  R  R  P  G  T  H  W  E  V  D  F  T  E  I  K

5181 CCAGGAATGTATGGATATAAATACCTCTTGGTGTTCATAGACACCTTCTCTGGCTGGGCCGAGGCTTACC 5250
      P  G  M  Y  G  Y  K  Y  L  L  V  F  I  D  T  F  S  G  W  A  E  A  Y  P
                                                                    ↓BamHI
5251 CCGCCAAACATGAAACAGCAAAAGTTGTTGCCAAGAAACTCTTAGAAGAAATTTTTCCCCGCTACGGGAT 5320
      A  K  H  E  T  A  K  V  V  A  K  K  L  L  E  E  I  F  P  R  Y  G  I

5321 CCCTCAGGTATTGGGTTCAGATAATGGACCCGCCTTTATCTCCCAGGTAAGTCAGTCTGTGGCCACCCTA 5390
       P  Q  V  L  G  S  D  N  G  P  A  F  I  S  Q  V  S  Q  S  V  A  T  L

5391 CTGGGGATTAATTGGAAGTTACATTGTGCATATCGACCCCAAAGTTCAGGTCAGGTAGAAAGAATGAATA 5460
      L  G  I  N  W  K  L  H  C  A  Y  R  P  Q  S  S  G  Q  V  E  R  M  N  R

5461 GATCAATTAAGGAGACTTTAACTAAAATTAACGCTAGAAACTGGCTCTAAGGATTGGGTGCTCCTCCTGCC 5530
       S  I  K  E  T  L  T  K  L  T  L  E  T  G  S  K  D  W  V  L  L  P

5531 CCTGGTTTTATACCGGGTACGTAACACGCCAGGCCCCCACGGGTTAACTCCTTTTGAAATCCTGTACGGG 5600
      L  V  L  Y  R  V  R  N  T  P  G  H  G  L  T  P  F  E  I  L  Y  G

5601 GCACCCCCACCTATGGCTCACTTCTTTGATACTGATATCTCTACGTTCGCTACCTCCCCCACTATGCAGG 5670
      A  P  P  P  M  A  H  F  F  D  T  D  I  S  T  F  A  T  S  P  T  M  Q  A
                      ↓PstI.
5671 CACATTTACGCGCCCTGCAGCTGGTCCAAGAAGAGATCCAGAGACCTCTAGCGGCGGCCTACCGAGAAAA 5740
       H  L  R  A  L  Q  L  V  Q  E  E  I  Q  R  P  L  A  A  A  Y  R  E  K

5741 GCTCGAAACCCCGGTTGTGCCTCACCCCTTCAAACCAGGAGACTCCGTCTGGGTTCGGAGACATCAAACC 5810
      L  E  T  P  V  V  P  H  P  F  K  P  G  D  S  V  W  V  R  R  H  Q  T
       ↓XhoI
5811 AAGAACCTCGAGCCACGGTGGAAAGGACCACATATCGTCCTCCTGACCACCCCCACAGCCTTAAAGGTAG 5880
      K  N  L  E  P  R  W  K  G  P  H  I  V  L  L  T  T  P  T  A  L  K  V  D
                                        ↓PstI
5881 ACGGAGTTGCTGCCTGGATTCACGCCTCCCATGTGAAAGCTGCAGGACCAACCACCAATCAAGACCTCTC 5950
      G  V  A  A  W  I  H  A  S  H  V  K  A  A  G  P  T  T  N  Q  D  L  S

5951 GGACAGCCCCAGCTCAGACGATCCATCGAGATGGAAAGTCCAACGCACCCAAAACCCTCTAAAGATAAGA 6020
      D  S  P  S  S  D  D  P  S  R  W  K  V  Q  R  T  Q  N  P  L  K  I  R
                                  M  E  S  P  T  H  P  K  P  S  K  D  K  T

6021 CTCTCTCGTGGAACTTAGTGTTTCTGGTGGGGATCTTATTCACAATAGACATAGGAATGGCCAATCCTAG 6090
      L  S  R  G  T
       L  S  W  N  L  V  F  L  V  G  I  L  F  T  I  D  I  G  M  A  N  P  S

6091 TCCACACCAAATATATAATGTAACTTGGGTAATAACCAATGTACAAACTAACACCCAAGCTAATGCCACC 6160
       P  H  Q  I  Y  N  V  T  W  V  I  T  N  V  Q  T  N  T  Q  A  N  A  T
```

*Fig. 1E*

```
6161  TCTATGTTAGGAACCTTAACCGATGTCTACCCTACCCTACATGTTGACTTATGTGACCTAGTGGGAGACA  6230
       S  M  L  G  T  L  T  D  V  Y  P  T  L  H  V  D  L  C  D  L  V  G  D  T

6231  CCTGGGAACCTATAGTCCTAAGCCCAACCAATGTAAAACACGGGGCACGTTACCCTTCCTCAAAATATGG  6300
       W  E  P  I  V  L  S  P  T  N  V  K  H  G  A  R  Y  P  S  S  K  Y  G

6301  ATGTAAAACTACAGATAGAAAAAACAGCAACAGACATACCCCTTTTACGTCTGCCCCGGACATGCCCCCC  6370
       C  K  T  T  D  R  K  K  Q  Q  Q  T  Y  P  F  Y  V  C  P  G  H  A  P

6371  TCGCTGGGGCCAAAGGGAACACATTGTGGAGGGGCACAAGATGGGTTTTGTGCCGCATGGGGATGTGAAA  6440
       S  L  G  P  K  G  T  H  C  G  G  A  Q  D  G  F  C  A  A  W  G  C  E  T
                ↓HindIII
6441  CCACCGGAGAAGCTTGGTGGAAGCCCTCCTCCTCATGGGACTATATCACAGTAAAAAGAGGGAGTAGTCA  6510
       T  G  E  A  W  W  K  P  S  S  S  W  D  Y  I  T  V  K  R  G  S  S  Q 6511  GGACAATAACTGTGAGGGAAAATGCAACCCCCTGATTTTGCAGTTCACCCAGAAGGGGAAACAAGCCTCT  6580
       D  N  N  C  E  G  K  C  N  P  L  I  L  Q  F  T  Q  K  G  K  Q  A  S 6581  TGGGACGGACCTAAGATGTGGGGATTGCGACTATACCGTACAGGATATGACCCTATCGCCTTATTCACGG  6650
       W  D  G  P  K  M  W  G  L  R  L  Y  R  T  G  Y  D  P  I  A  L  F  T  V 6651  TATCCCGGCAGGTGTCAACCATTACGCCGCCTCAGGCAATGGGACCAAACCTAGTCTTACCTGATCAAAA  6720
       S  R  Q  V  S  T  I  T  P  P  Q  A  M  G  P  N  L  V  L  P  D  Q  K 6721  ACCCCCATCCCGACAATCTCAAACAGGTCCCAAAGTGGCGACCCAGAGGCCCCAAACGAATGAAAGCGCC  6790
       P  P  S  R  Q  S  Q  T  G  P  K  V  A  T  Q  R  P  Q  T  N  E  S  A 6791  CCAAGGTCTGTTGCCCCCACCACCGTGGGTCCCAAACGGATTGGGACCGGAGATAGGTTAATAAATTTAG  6860
       P  R  S  V  A  P  T  T  V  G  P  K  R  I  G  T  G  D  R  L  I  N  L  V 6861  TACAAGGGACATACCTAGCCTTAAATGCCACCGACCCCAACAAAACTAAAGACTGTTGGCTCTGCCTGGT  6930
       Q  G  T  Y  L  A  L  N  A  T  D  P  N  K  T  K  D  C  W  L  C  L  V 6931  TTCTCGACCACCCTATTACGAAGGGATTGCAATCTTAGGTAACTACAGCAACCAAACAAACCCTCCCCCA  7000
       S  R  P  P  Y  Y  E  G  I  A  I  L  G  N  Y  S  N  Q  T  N  P  P  P 7001  TCCTGCCTATCTATTCCGCAACACAAGCTGACCATATCTGAAGTATCAGGGCAAGGACTGTGCATAGGGA  7070
       S  C  L  S  I  P  Q  H  K  L  T  I  S  E  V  S  G  Q  G  L  C  I  G  T 7071  CTGTTCCTAAGACCCACCAGGCTTTGTGCAATAAGACGCAACAGGGACATACAGGGGCGCACTATCTAGC  7140
       V  P  K  T  H  Q  A  L  C  N  K  T  Q  Q  G  H  T  G  A  H  Y  L  A 7141  CGCCCCCAATGGCACCTATTGGGCCTGTAACACTGGACTCACCCCATGCATTTCCATGGCGGTGCTCAAT  7210
       A  P  N  G  T  Y  W  A  C  N  T  G  L  T  P  C  I  S  M  A  V  L  N 7211  TGGACCTCTGATTTTTGTGTCTTAATCGAATTATGGCCCAGAGTGACTTACCATCAACCCGAATATGTGT  7280
       W  T  S  D  F  C  V  L  I  E  L  W  P  R  V  T  Y  H  Q  P  E  Y  V  Y 7281  ACACACATTTTGCCAAAGCTGTCAGGTTCCGAAGAGAACCAATATCACTAACTGTTGCCCTCATGTTGGG  7350
       T  H  F  A  K  A  V  R  F  R  R  E  P  I  S  L  T  V  A  L  M  L  G
```

*Fig. 1F*

```
                            ↓SacII
7351  AGGACTCACTGTAGGGGGCATAGCCGCGGGGGTCGGAACAGGGACTAAAGCCCTCCTTGAAACAGCCCAG  7420
       G  L  T  V  G  G  I  A  A  G  V  G  T  G  T  K  A  L  L  E  T  A  Q

7421  TTCAGACAACTACAAATGGCCATGCACACAGACATCCAGGCCCTAGAAGAGTCAATTAGTGCCTTAGAAA  7490
       F  R  Q  L  Q  M  A  M  H  T  D  I  Q  A  L  E  E  S  I  S  A  L  E  K

7491  AGTCCCTGACCTCCCTTTCTGAAGTAGTCTTACAAAACAGACGGGGCCTAGATATTCTATTCCTACAAGA  7560
        S  L  T  S  L  S  E  V  V  L  Q  N  R  R  G  L  D  I  L  F  L  Q  E

7561  GGGAGGGCTCTGTGCCGCATTAAAAGAAGAATGTTGCTTCTATGCGGATCACACCGGACTCGTCCGAGAC  7630
       G  G  L  C  A  A  L  K  E  E  C  C  F  Y  A  D  H  T  G  L  V  R  D

7631  AATATGGCTAAATTAAGAGAAAGACTAAAACAGCGGCAACAACTGTTTGACTCCCAACAGGGATGGTTTG  7700
       N  M  A  K  L  R  E  R  L  K  Q  R  Q  Q  L  F  D  S  Q  Q  G  W  F  E

7701  AAGGATGGTTCAACAGGTCCCCCTGGTTTACAACCCTAATTTCCTCCATTATGGGCCCCTTACTAATCCT  7770
       G  W  F  N  R  S  P  W  F  T  T  L  I  S  S  I  M  G  P  L  L  I  L

7771  ACTCCTAATTCTCCTCTTCGGCCCATGCATCCTTAACAGATTAGTACAATTCGTAAAAGACAGAATATCT  7840
       L  L  I  L  L  F  G  P  C  I  L  N  R  L  V  Q  F  V  K  D  R  I  S

7841  GTGGTACAAGCCTTAATTTTAACCCAACAGTACCAACAGATAAAGCAATACGATCCGGACCGACCATGAT  7910
       V  V  Q  A  L  I  L  T  Q  Q  Y  Q  Q  I  K  Q  Y  D  P  D  R  P  *

7911  TTCCAATTAAATGTATGATTCCATTTAGTCCCCAGAAAAAGGGGGGAATGAAAGACCCCCTACCCAAAAT  7980
                 ↓PstI
7981  TTAGCCAGCTACTGCAGTGGTGCCATTTCACAAGGCATGGAAAATTACTCAAGTATGTTCCCATGAGATA  8050

8051  CAAGGAAGTTAGAGGCTAAAACAGGATATCTGTGGTTAAGCACCTGGGCCCCGGCTTGAGGCCAAGAACA  8121

8121  GTTAAACCCCGGATATAGCTGAAACAGCAGAAGTTTCAAGGCCGCTGCCAGCAGTCTCCAGGCTCCCCAG  8190

8191  TTGACCAGAGTTCGACCTTCCGCCTCATTTAAACTAACCAATCCCCATGCCTCTCGCTTCTGTACGCGCG  8260
                                                                    ↓SmaI
8261  CTTTCTGCTATAAAACGAGCCATCAGCCCCCAACGGGCGCGCAAGTCTTTGCTGAGACTTGACCGCCCCG  8330
      ↓KpnI
8331  GGTACCCGTGTACGAATAAACCTCTTGCCGATTGCATCTGACTCGTGGTCTCGGTGTCCGTGGGCGCGG  8400

8401  GGCCTCATCGCCGAGGAAGACCCAGTTCGGGGGTCTTTCA  8440
```

*Fig. 1G*

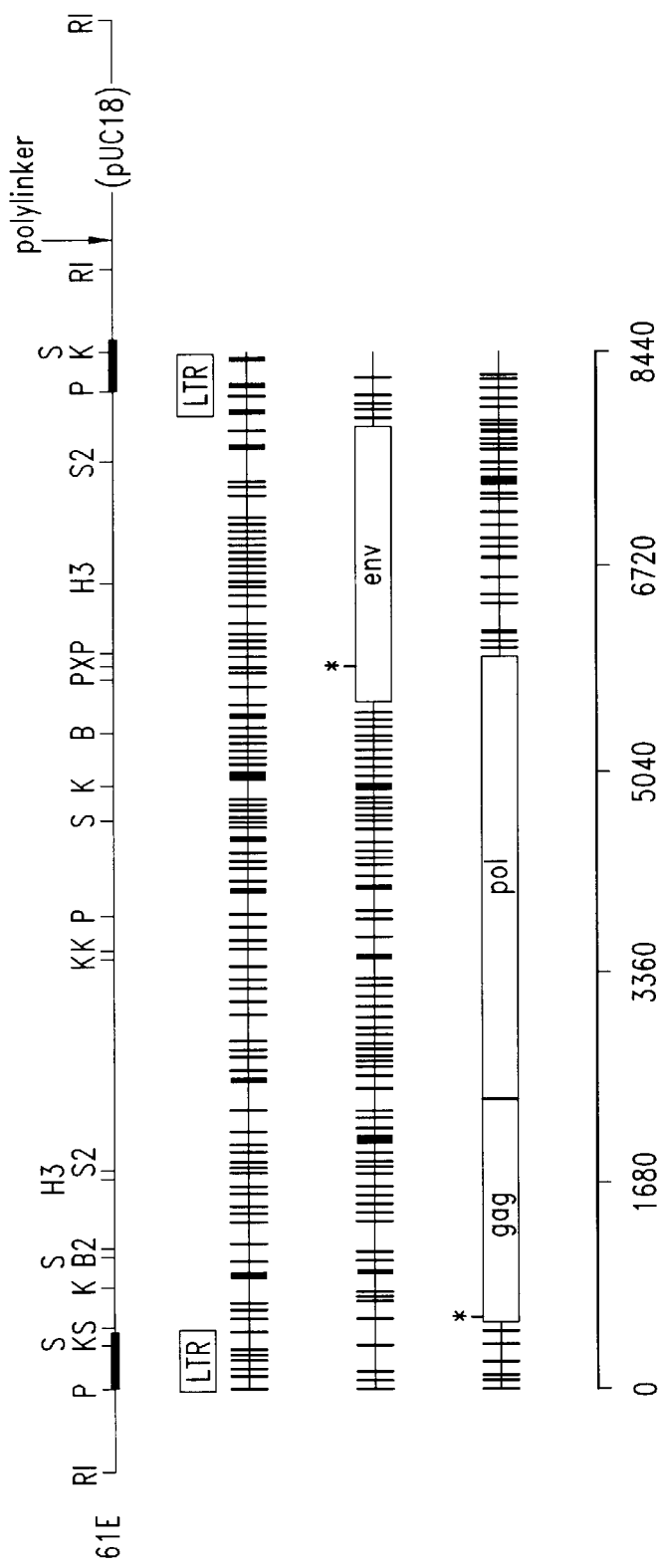
Fig. 2A
Fig. 2B

```
                                              |leader>
61C                    T              A
61E  5958 CCCAGCTCAGACGATCCATCGAGATGGAAAGTCCAACGCACCCAAAACCCTCTAAA
                                    M  E  S  P  T  H  P  K  P  S  K 61C
61E  GATAAGACTCTCTCGTGGAACTTAGTGTTTCTGGTGGGGATCTTATTCACAATAGACATA
      D  K  T  L  S  W  N  L  V  F  L  V  G  I  L  F  T  I  D  I
            |GP70>           Pro   Met
61C                           C     G
61E  GGAATGGCCAATCCTAGTCCACACCAAATATATAATGTAACTTGGGTAATAACCAATGTA
      G  M  A  N  P  S  P His Q Ile Y  N  V  T  W  V  I  T  N  V 61C          C
61E  CAAACTAACACCCAAGCTAATGCCACCTCTATGTTAGGAACCTTAACCGATGTCTACCCT
      Q  T  N  T  Q  A  N  A  T  S  M  L  G  T  L  T  D  V  Y  P Met
61C                                                           G
61E  ACCCTACATGTTGACTTATGTGACCTAGTGGGAGACACCTGGGAACCTATAGTCCTAAGC
      T  L  H  V  D  L  C  D  L  V  G  D  T  W  E  P Ile V  L  S

- - - - - - Gly       Pro
                   ------------------G G      C
61E  CCAACCAATGTAAAACACGGGGCACGTTACCCTTCCTCAAAATATGGATGTAAAACTACA
      P  T AsnValLysHisGlyAlaArg Y  P Ser S  K  Y  G  C  K  T  T

61C             G
61E  GATAGAA 6320..//..6965 TTAGGTAACTACAGCAACCAAACAAACCCTCCCCCAT
      D  R                      L  G  N  Y  S  N  Q  T  N  P  P  P

Ile         Pro
61C        A           C
61E  CCTGCCTATCTATTCCGCAACACAAGCTGACCATATCTGAAGTATCAGGGCAAGGACTGTG
      S  C Leu S  I  P Gln H  K  L  T  I  S  E  V  S  G  Q  G  L  C 61C
61E  CATAGGGACTGTTCCTAAGACCCACCAGGCTTTGTGCAATAAGACGCAACAGGGACATACA
      I  G  T  V  P  K  T  H  Q  A  L  C  N  K  T Gln Q  G  H  T

AspTyrLeuThrAlaProArg
61C        G  TATCTAACCGCCCCGCGG
61E  GGGGCGCAC                  TATCTAGCCGCCCCCAATGGCACCTATTGGGCCT
      G  A His                    Y  L  A  A  P  N  G  T  Y  W  A
```

*Fig. 3A*

```
                                                                    Leu
61C                                                                  T
61E  GTAACACTGGACTCACCCCATGCATTTCCATGGCGGTGCTCAATTGGACCTCTGATTTTTG
      C  N  T  G  L  T  P  C  I  S  M  A  V  L  NTrp T  S  D  F  C 61C
61E  TGTCTTAATCGAATTATGGCCCAGAGTGACTAACCATCAACCCGAATATGTGTACACACAT
        V  L  I  E  L  W  P  R  V  T  Y  H  Q  P  E  Y  V  Y  T  H

Gly              |p15E>                           |LTR
61C          G                 G
61E  TTTGCCAAAGCTGTCAGGTTCCGAAGAGAACCAATA 7324..//..7956 GAATGAAAG
      F  A  K  AVal R  F  R  R  E  P  I

U3>
61C
61E  ACCCCCTACCCAAAATTTAGCCAGCTACTGCAGTGGTGCCATTTCACAAGGCATGGAAAAT

61C                                    G
61E  TACTCAAGTATGTTCCCATGAGATACAAGGAAGTTAGAGGCTAAAACAGGATATCTGTGGT

61C                                                         A
61E  TAAGCACCTGGGCCCCGGCTTGAGGCCAAGAACAGTTAAACCCCGGATATAGCTGAAACAG 61C
61E  CAGAAGTTTCAAGGCCGCTGCCAGCAGTCTCCAGGCTCCCCAGTTGACCAGAGTTCGACCT 61C
61E  TCCGCCTCATTTAAACTAACCAATCCCCATGCCTCTCGCTTCTGTACGCGCGCTTTCCTGC

61C
                              - |R>
61E  TATAAAACGAGCCATCAGCCCCCAACGGGCGCGCAAGTCTTTGCTGAGACTTGACCGCCCC

61C                                  |U5>
61E  GGTACCCGTGTACGAATAAACCTCTTGCCGATTGCATC../..8440
```

*Fig. 3B*

PROTOTYPE FELV ISOLATES FOR USE IN DISEASE MODELS AND VACCINES

CROSS-REFERENCE TO RELATED APPLICATIONS

This application is a division of U.S. patent application Ser. No. 07/939,554, filed Sep. 1, 1992, now abandoned, which is a continuation of U.S. patent application Ser. No. 07/284,139, filed Dec. 13, 1988 now abandoned.

TECHNICAL FIELD

The present invention is generally directed toward the derivation of molecular clones of FeLV and their use as vaccines and in disease models.

BACKGROUND OF THE INVENTION

Retroviruses form a large class of enveloped RNA viruses which invade a large number of specific mammalian hosts. They are infectiously transmitted by a variety of mechanisms, are frequently associated with severe diseases, and share common elements among their structures. The retroviruses, consisting of a (+) strand RNA dimer (ssRNA), form long terminal repeats ("LTR") in their proviral DNA intermediates and a genome coding for capsid proteins ("the gag gene"), reverse transcriptase and integrase functions (the "pol" gene), and the membrane envelope gene ("env"). With particular viruses, other open reading frames have been shown to be present coding for proteins having specific functions in addition to the functions of the common genes.

Feline leukemia viruses (FeLV) are exogenous type C retroviruses that are responsible for induction of a diverse series of lymphoreticular diseases of outbred cats including lymphosarcoma, leukemia, aplastic anemia, myelodysplasia, and feline acquired immunodeficiency syndrome (Hardy et al., *Cancer Res.* 36:582, 1976; Hardy, *Feline Leukemia Virus,* Hardy, Essex, McCelland, eds. (Elsevier/North Holland, 1980), pp. 3–31; Hoover, Rojko, Olsen, *Feline Leukemia,* Olsen, ed. (CRC Press, Boca Raton, Fla., 1980), pp. 32–51; Hardy and Essex, *Prog. Allergy* 37:353, 1986). The genome of FeLV is a 60–70S dimer of single-stranded RNA consisting of a gag gene encoding the capsid proteins, a pol gene encoding the protease, reverse transcriptase and integrase, and an env gene encoding the gp70 and p15E viral envelope proteins. As with other retroviruses, when a susceptible cell is infected with FeLV (in vivo or in vitro), the genome is transcribed into a double-stranded DNA copy which is then carried in the cellular DNA as a provirus organized into 5'-LTR (long terminal repeat)-gag-pol-env-LTR-31' regions. The integrated provirus then serves as the template for production of FeLV RNAs and ultimately infectious virions.

FeLV have been classified into subgroups A, B, and C on the basis of virus interference and neutralization assays, and the distribution of the subgroups within feline populations differs markedly. Subgroup A viruses have been found in all naturally occurring infections examined, either alone or in combination with B and C. Subgroup B, found in approximately 40% of all infections, and subgroup C, found in perhaps 1% of infections, occur as mixed infections of subgroups A and B, A and C, or A, B, and C. Subgroup identity also correlates with the host range of infection in vitro and pathogenicity in cats: FeLV-A isolates are sometimes restricted to growth in feline cells and are minimally pathogenic; FeLV-B isolates grow in heterologous cells such as human and canine fibroblastoid cells and are found at a higher frequency in cats with proliferative disease; and the rare FeLV-C isolates have an extended host range including human, canine, and guinea pig cells and are capable of inducing aplastic anemia.

In view of the devastating effect of FeLV-induced disease in domestic cats, the prevention of FeLV infection through vaccination of susceptible animals is a high priority for veterinary researchers. Numerous attempts to produce such a vaccine have been largely unsuccessful and, in fact, the only commercially available vaccine (Leukocell™, Norden Laboratories, Lincoln, Nebr.) has been severely criticized for its questionable efficacy (Pedersen et al., *Feline Practice* 15:7–20, 1985). The present invention fulfills the need in the art for a suitable FeLV vaccine, and further provides other related advantages, including the definition of a prototype highly infectious FeLV-A challenge virus, a prototype molecularly cloned immunodeficiency inducing FeLV, and a disease model useful for the study of retrovirus-induced immunodeficiency syndrome and leukemia in cats and humans.

DISCLOSURE OF INVENTION

Briefly stated, the present invention discloses molecular clones of feline leukemia virus isolates that encode (a) a prototype highly infectious, minimally pathogenic virus, (b) a variant genome that is replication-defective and associated with a fatal immunodeficiency in cats similar to AIDS (Hoover, *Blood* 70: 1880–1892, 1987; Overbaugh et al., *Science* 239:906–910, 1988), and (c) a chimeric genome that is replication-competent and induces the immunodeficiency syndrome described above. More specifically, these molecular clones are used to generate cell lines producing infectious virus which is useful in the preparation of vaccines or the generation of viremia or disease challenge systems.

In one aspect of the present invention, an isolated DNA sequence encoding the proviral genome of a FeLV-A subtype or a biological derivative thereof is disclosed. For purposes of the present invention, FeLV-A subtype or "biological derivative thereof" includes mutants of an FeLV-A subtype which are at least 92% homologous to a FeLV-A subtype. Within certain embodiments, the DNA sequence may be derived from proviral molecular clone 61C, which is replication-defective and not capable of inducing viremia in feline species (*Felis domestica*), or clones 61E or EECC, which are capable of inducing persistent viremia in feline species.

Recombinant plasmids capable of directing the expression of the proviral genome of a FeLV-A subtype or biological derivative thereof, and mammalian cells transfected with such a recombinant plasmid are also disclosed. Suitable mammalian cells include feline cells, such as AH927, CRFK, FCWF, Fc9, feline embryo fibroblasts or primary feline cell cultures, and mink lung cells.

Within another aspect of the present invention, a method of producing a FeLV-A subtype or biological derivative thereof is disclosed. The method generally comprises: (a) transfecting a mammalian host cell with a recombinant plasmid capable of directing the expression of the proviral genome of a FeLV-A subtype or biological derivative thereof, the plasmid comprising a DNA sequence encoding the proviral genome of a FeLV-A subtype or biological derivative thereof; (b) growing the host cell in an appropriate medium; and (c) separating the FeLV-A subtype or biological derivative thereof from the host cells. Suitable DNA sequences include those derived from clones 61E and EECC. Within an alternative embodiment, the mammalian host cell is cotransfected with a recombinant plasmid as briefly described above, the plasmid comprising a DNA sequence derived from the clone 61C and a DNA sequence encoding a replication-competent proviral genome, such as a DNA sequence derived from the clone 61E. The methods may also include, after the step of separating, purifying the FeLV-A subtype or biological derivative thereof by methods well known in the art.

Within a related aspect of the present invention, a method of producing a FeLV vaccine is disclosed. The method generally comprises: (a) transfecting a mammalian host cell with a recombinant plasmid capable of directing the expression of the proviral genome of a FeLV-A subtype or biological derivative thereof; (b) growing the host cell in an appropriate medium; (c) harvesting the FeLV-A subtype or biological derivative immunogens; and (d) inactivating the FeLV-A subtype or biological derivative thereof. Within an alternative embodiment, the mammalian host cell is cotransfected as described above. The FeLV-A subtype or biological derivative thereof may be inactivated in a number of ways, including exposure to formalin, beta-propriolactone or binary ethyleneimine (BEI) under conditions and for a time sufficient to cause inactivation. The method may also include, after the step of inactivating, concentrating the FeLV-A subtype to achieve an antigenic mass suitable for clinical administration to provide protection in the feline species.

The present invention also discloses methods for protecting a feline host from FeLV infection. In one such method, an immunogenically effective amount of a composition comprising an inactivated FeLV-A subtype or biological derivative thereof in combination with a physiologically acceptable carrier or diluent is administered to the feline host. Suitable carriers or diluents include sterile water and phosphate buffered saline. The composition may also include a suitable adjuvant, such as complete or incomplete Freund's adjuvant, RIBI (adjuvant), oil adjuvants, particulate adjuvants such as aluminum hydroxide and aluminum phosphate, or general immune stimulating adjuvants, such as avridine and ama 31–91. In one aspect of the present invention, the physiologically acceptable carrier or diluent comprises cell-free supernatant derived from FeLV-A subtype-producing cells. In this regard, the physiologically acceptable carrier or diluent may further include whole cell lysates of FeLV-A subtype-producing cells. Within a related method, an immunogenically effective amount of a composition comprising the env gene product of a FeLV-A subtype is administered in combination with a physiologically acceptable carrier or diluent.

As noted above, the present invention discloses vaccines against FeLV-induced disease. In one aspect of the present invention, the vaccine comprises an inactivated FeLV-A subtype or biological derivative thereof in combination with a suitable adjuvant. Within preferred embodiments, the FeLV-A subtype or biological derivative thereof is encoded by a DNA sequence derived from clone EECC or clone 61E.

Within another aspect of the present invention, the vaccine comprises a FeLV-A subtype encoded by a DNA sequence derived from a FeLV clone which is replication competent, such as clone 61E, in combination with a biological derivative of a FeLV-A subtype encoded by a DNA sequence derived from clone 61C, along with a physiologically acceptable carrier or diluent.

In yet another aspect of the present invention, feline hosts exhibiting fatal immunodeficiency disease induced by inoculation with a FeLV-A subtype or biological derivative thereof are disclosed. These feline hosts are useful as disease models for both cats and other mammals, including humans.

These and other aspects of the present invention will become evident upon reference to the following detailed description and attached drawings.

BRIEF DESCRIPTION OF THE DRAWINGS

FIG. 1 is a depiction of the complete nucleotide sequence of clone 61E. The sequence begins at the 5'LTR and extends to the 3'LTR corresponding to the 8440 nucleotide region shown schematically in FIG. 2. Deduced amino acid sequences of the two major open reading frames (ORFs) are designated by a single letter code beneath the DNA sequence. Restriction sites also noted in FIG. 2 are shown above the DNA sequence.

FIG. 2A is a restriction site map of clone 61E with location of open reading frames (ORFs). From top to bottom frames 1 to 3 are represented. Vertical bars ( ) mark positions of termination codons. Boxes ( ) represent the ORFs known to encode viral proteins and the positions of the likely initiating methionines for the gag (gag-pol) and env translation products. Restriction sites indicated correspond to BamHI(B), BelII(B2), EcoRI(RI), HindIII(H3), KpnI(K), PstI(P), SmaI(S), SstII(S2), and XhoI(X). A restriction enzyme map of clone 61C is shown in FIG. 2B. Only divergent sites are indicated in the map of the variant clone.

FIG. 3 is a depiction of the nucleotide sequence of the env-3'LTR of 61C and comparison to the corresponding region of molecular clone 61E. Portions of the nucleotide sequence of 61E are shown along with the single letter translation of the env protein. The corresponding sequence of clone 61C was determined and only those nucleotide amino acids that differ are shown here. Two stretches of complete nucleotide identity are not shown and are indicated by ..//... Where differences result in a change in the deduced amino acid sequence, the three-letter amino acid code is shown. Dashes indicate gaps.

FIG. 4*a* is a depiction of plasmid pUC18-61E.

FIG. 4*b* is a depiction of plasmid pUC18-61C.

FIG. 4*c* is a depiction of plasmid pUC18-EECC.

DETAILED DESCRIPTION OF THE INVENTION

As noted above, the subject invention is concerned with methods and compositions for protecting feline hosts from FeLV infection, particularly by providing infectious proviral molecular clones which encode a FeLV of the A subtype or a biological derivative thereof. When certain clones, such as clone 61E, are used to transfect feline cells in vitro, such transfected cells produce infectious virus which is not cytopathic for feline T-lymphocytes or fibroblastoid cells. The growth of this virus is restricted to feline cells (and is therefore ecotropic). Virus derived from these cells is shown herein to infect specific pathogen-free cats from weanling to adult age. None of these cats has developed disease more than one year postinoculation, although they have developed persistent virus infection. Thus, the FeLV-A proviral genome encodes a prototype, ecotropic, horizontally transmissible, and minimally pathogenic feline leukemia virus. It may be distinguished from other feline leukemia viruses, in part, by its ability to consistently induce viremia in cats other than newborn age, thereby mimicking FeLV found in nature more appropriately than any other strain disclosed thus far. The nucleotide sequence of its envelope gene is very highly conserved with other strains of FeLV which are also easily transmitted and found in all FeLV-infected cats in nature. Therefore, an immune response generated to the FeLV-A based vaccines of the present invention is expected to protect against virtually any other feline leukemia virus horizontally transmissible in nature. Furthermore, because of the unique capacity of the virus encoded by DNA sequences derived from clones 61E or EECC to induce a high incidence of viremia in cats inoculated with 61E or EECC, a valid challenge system is provided which proves protection against a homologous virus challenge.

The subject invention is also concerned with methods and compositions for providing a relevant disease model in feline species that may be used to further prove an effective FeLV vaccine (i.e., protection against disease) or that may be used to study possibilities of prophylaxis and therapy of related immunodeficiencies in other species (e.g., human immunodeficiency virus infection in man). The FeLV proviral molecular clone 61C is not infectious, but, when transfected into feline cells, can be rescued by subsequent transfection of molecular clone 61E or infection with 61E virus. The resulting mixture of 61E and 61C virus, when inoculated into 8-week-old susceptible cats, induces a fatal immunodeficiency disease within four months that is typical of that observed in cats inoculated with the original FeLV-FAIDS isolate (Hoover, *Blood* 70:188–1892, 1987; Overbaugh, *Science* 239:906–910, 1988). Additionally, a chimeric FeLV proviral molecular clone may be constructed (EECC) by exchanging portions of the 61E and 61C genome. When such a construct is transfected into susceptible feline cells, the resulting virus (FeLV-EECC) is replication competent and induces immunodeficiency disease.

Within preferred embodiments for producing replication competent viruses, FeLV-61E-A and FeLV-EECC provirus are transfected into an appropriate cellular host in culture, for example, the CRFK [ATCC# CCL94] or AH927 cell line (Overbaugh, *Science* 239:906–910, 1988), conveniently as a provirus plasmid with or without a selectable marker. Methods of transfection may include DEAE dextran precipitation, calcium phosphate precipitation, or electroporation. As a result of the introduction of the proviral DNA, the proviral genome will become integrated into the cellular genome. The transfected cells are selected, expanded and screened for reverse transcriptase, viral production, the level of viral protein antigen released, and any other characteristics associated with the use of the virus as a vaccine.

For producing replication defective viruses, such as FeLV-61C, the proviral genome is transfected into an appropriate cellular host in culture and the resulting transformed line is cotransfected or coinfected with a replication competent proviral genome or virus, such as FeLV-61E.

Stably transfected cell lines which constitutively express FeLV protein and viruses are grown to 100% confluency in 150 cm$^2$ roller bottles by seeding, for example, with a minimum of 5–6×10$^7$ cells/roller bottle containing 250 ml cell growth medium. After cells have reached confluency in 3–7 days, the cell growth medium is discarded and the cells are replenished, for example, with 250 ml virus growth medium. The cells are further incubated, normally at 37° C., for one to several days and the FeLV containing medium is harvested. Multiple harvest, preferably a minimum of five times, is allowed until the cell monolayer begins to detach from the bottles. The FeLV harvest materials may be concentrated up to 100× depending on virus titer and/or antigenic content, as described for virus fluids. Inactivation, concentration, and adjuvanting of the cell line fluids proceeds as for virus fluids and is described herein.

Once a suitable FeLV-A subtype or biological derivative thereof has been prepared, the feline host may be inoculated by any convenient means with a sufficient amount of the inactivated virus produced from cloned proviral DNA, or with the virus and cell substrate mixtures in order provide an appropriate immune response. The amount of virus utilized will generally be from about 10$^4$ to about 5×10$^6$, usually about 1–5×10$^5$ focus-forming units/kg host (FFU/kg). The virus may be in any convenient physiologically acceptable medium, e.g., sterile water, phosphate-buffered saline, growth medium or the like. Generally, the dosage volume will be about 0.5 to 2.0 ml, and is administered by injection subcutaneously, intramuscularly, intraperitoneally, intravenously or the like. The vaccines of the present invention may be administered to previously primed hosts. One or more booster injections may be employed at weekly to six-week, usually two- to four-week, intervals.

To summarize the examples which follow, the F6A virus-encoding proviral clone 61E was derived directly from intestinal tissue DNA of a specific-pathogen-free cat following inoculation with lymphosarcoma cell-free supernatant from a pet cat with a naturally occurring feline lymphosarcoma from Fort Collins, Colorado. To obtain clones with intact proviruses, DNA from cat 1161 was first cleaved with EcoRI (which does not cleave within the FeLV genome) and fractionated on a sucrose gradient. Fractions containing DNA of sufficient length to potentially contain full-length proviruses, but within the capacity of the bacteriophage vector gtWES B (P. Leder, D. Tiemeier, L. Enquist, *Science* 196:175, 1977), were pooled. The libraries were prepared and screened with an exogenous LTR-specific probe (Mullins et al., *Nature* 319:333–336, 1984). An EcoRI fragment of the full-length F6A provirus and host flanking sequences was subcloned into pUC18. Deletion clones were then generated by digestion with exonuclease BAL31, ligated into M13mp18, and sequenced by the dideoxy chain termination method. The complete 8,440 base pair (bp) sequence of the F6A provirus is shown in FIG. 1 as well as the deduced amino acid sequences of the two long open reading frames. A simplified restriction map with the location of open reading frames (ORFs) corresponding to gag (encoding the nucleocapsid proteins), pol (encoding protease, reverse transcriptase, and endonuclease-integrase) and env (encoding the extracellular [gp70] and transmembrane [p15E] envelope proteins) within the F6A sequences is shown in FIG. 2. The probable initiating methionines (ATG) of the gag and env genes occur at nucleotide positions 906 and 5981, respectively. In general, the F6A proviral sequences reflect a typical type C retrovirus genome. Particulars of the sequence are discussed in Donahue et al. (*J. Virol.* 162:722–731, 1988). Relevant to the present invention, it is significant that when the deduced gp70 protein of F6A is compared to that of two other type A isolates, F3A and FGA (Glasgow), they share remarkedly strong (98%) homology, despite their isolation from naturally infected cats up to 13 years apart and from widely separate geographic locations: FGA was isolated in Glasgow, Scotland, in 1970 and carried in culture for several years before being subjected to molecular cloning; F3A was isolated in New York City in 1977 (E. Zuckerman and W. D. Hardy, Jr., personal communication) and was also extensively propagated in culture before being cloned; and F6A was molecularly cloned from cat tissue DNA after one in vivo passage of a virus isolated from a pet cat in 1983 and was never propagated in vitro before being cloned. All three proviruses were molecularly cloned and sequenced. This remarkable sequence conservation may reflect stringent selection against antigenic changes in the ubiquitous, viremia-inducing and horizontally transmissable form of FeLV. This sequence data and comparison, together with the biological activity of F6A described below, show that F6A represents a prototype of the highly conserved, horizontally transmitted, minimally pathogenic subgroup A form of FeLV that is probably present in all naturally infected cats.

To define the biological activity of F6A, a feline embryo fibroblast cell line (AH927) was transfected with cloned 61E DNA. Reverse transcriptase (RT) was detected in the cultures by 12 days, as was proviral DNA. Sixteen 8-week old SPF cats were then inoculated with $10^5$ focus-forming units of 61E-derived F6A virus (titered by clone 81 assay, see below) derived from transfected cells. Each inoculated cat became viremic within two to four weeks and each has remained viremic since then. None has developed any signs of immunodeficiency disease after 10 months to more than 2 years. One cat developed a $T^-$ cell lymphosarcoma after 21 months but the others remain healthy, indicating that F6A is minimally pathogenic, although highly infectious, and, like other chronic retroviruses, is capable of inducing lymphosarcoma with a long latency.

The following examples are offered by way of illustration and not by way of limitation.

EXAMPLES

Example I

Generation of FeLV Subtype A-Producing Cell Lines by Gene Transfer of a Molecular Clone into Susceptible Feline Cells To provide for a vaccine, the FeLV-61E-A provirus was isolated as an EcoRI fragment (FIG. 3) and subcloned into the EcoRI site of pUC18 (FIG. 4). The resulting plasmid (pUC18-61E) was introduced into the AH927 feline embryo fibroblast cell line by transfection according to the electroporation procedure described by Potter et al. (*Proc. Natl. Acad. Sci. (USA)* 81:7161–7165, 1984).

The titer of infectious F6A virus released from AH927-61E was found to vary from 4–8×$10^6$ ffu/ml (Lee et al., *J. Natl. Cancer Inst.* 49:55–60, 1972).

Example II

The following description represents procedures suitable for the inactivation, concentration, and adjuvanting of cell line fluids and virus fluids within the present invention.

Binary Ethyleneimine (BEI) Inactivation of Virus Fluids or Cell Line Fluids Equal volumes of a 0.2 molar bromoethlamine hydrobromide solution and a 0.4 molar sodium hydroxide solution are mixed and incubated at about 37° C. for 60 min. The resulting cyclized inactivant is binary ethyleneimine (BEI) which is added to the virus fluids or cell line fluids at 0.5 to 4%, volume to volume. THe inactivating virus or cell line fluids are held from 4°–37° C. for 24 to 72 hr under periodic agitation.

The inactivated virus or cell line fluids are passaged three times in cell culture and examined for specific virus growth to test for complete inactivation.

Concentration of Virus or Cell Culture Fluids

The virus or cell line fluids may be concentrated from 2 to 100 times by any number of available techniques such as Amicon, pellicon (Millipore) concentrating devices, precipitation techniques, such as ammonium chloride or polyethylene glycol (PEG), concentration with Carbowax liquid or wax in conjunction with dialysis tubing, or adjuvant concentration techniques, such as with aluminum phosphate. For the PEG concentration method, 80 ml of 50% PEG is added to 1 liter of virus or cell line fluids, then mixed overnight at 4° C. The next day the PEG-virus fluids are centrifuged at >2500 RPM, the supernatant is discarded, and the PEG-virus pellet is resuspended in the correct volume of media to achieve the desired concentration.

Adjuvanting Virus or Cell Culture Fluids

The following adjuvants may be used separately or in combination with 2 or more adjuvants depending on interdermal induration reactions in animals and adjuvant mixing compatability.

Ethylene maleic anhydride (EMA) prepared at a 1% weight to volume concentration in water is added to the inactivated virus or cell line fluids at 0.01% to 6% volume to volume (concentration separately or in combination with other adjuvants). The pH of the resulting fluids is adjusted to 7.1 to 7.7 by addition of 1 N sodium hydroxide.

Neocryl A640 is a trade name for a latex emulsion of a copolymer (A or styrene and a mixture of acrylic acid and methacrylic acid). Neocryl A640 is an uncoalesced aqueous acrylic copolymer with styrene, having pH 7.5, viscosity 100 cps (Brookfiled 25° C.), weight per gallon is 8.6 lbs as supplied containing 40% solids by weight and 38% solids by volume. The numeral A640 denotes a grade thereof. Other useful Neocryl grades are 520, 625, and 966. The term "CSMA" is used hereinafter to refer to a copolymer of styrene and a mixture of acrylic acid and methacrylic acid. CSMA prepared in a 50% volume per volume suspension in water is added to the inactivated virus or cell line fluids from 0.2 to 10% volume separately or in combination with other adjuvants. Usually there is no need for pH adjustment since the CSMA is a neutral pH.

Modern Veterinary Products (Omaha, Nebr.) Emulsigen adjuvant for small animals is an oil-in-water emulsion which is used separately or in combination with other adjuvants in a 1 to 20% volume to volume of virus or cell line fluids.

Avridine is used separately or in combination with other adjuvants at from 5 to 30 mg per dose. Avridine at 2.4 gm is dissolved in 18 ml of absolute ethyl alcohol, then 1.8 ml of Tween-80 is added and the mixture is passed through a 0.2 micron filter. Subsequently, 20.2 ml of Intralipid soy bean oil is asceptically added to the avridine. Seven to 50% of this adjuvant is then added volume to volume to the virus or cell line fluids.

Raw or purified saponin is used separately or in combination with other adjuvants at from 0.05 mg to 5 mg per dose. Saponin is prepared at a 200 mg/ml concentration, filter sterilized and then added to the virus or cell line fluids at from 0.05 to 20% volume to volume.

Aluminum phosphate at from 0.01 to 5 mg per dose or aluminum hydroxide at from 0.5 to 20 mg per dose may also be used separately or in combination with other adjuvants.

Cell and Virus Growth Medium

In vaccine production, cells may be grown in minimal essential media (MEM) supplemented with vitamins, nonessential amino acids, sodium pyruvate, sodium bicarbonate (Gibco, Grand Island, N.Y.) containing 10–25 mM Hepes buffer, 30 g/ml polymyxin and 30 g/ml neomycin which has been filter sterilized and stored at 4C. Prior to addition to cells, 2 mM L-glutamine and bovine serum is added to the medium. For cell growth, the bovine serum is added to 10%. For cell maintenance, the bovine serum is added to 0.05%. The average harvest is preferably greater than $10^4$ particles/ml.

Example III

Use of F6A Virus from the AH927-61E Cell Line as a Vaccine Utilizing Freund's Adjuvant For purposes of vaccine preparation, AH927-61E cells were grown as follows. F6A virus containing cell supernatants ($2\times10^5$ ffu/ml) were collected, in some instances concentrated, and inactivated with 0.1%–2% formalin or binary ethylene imine (BEI). Inactivated viral preparations were formulated with complete or incomplete Freund's adjuvant and delivered to SPF cats in 1 ml (?) intramuscular inoculations.

For the studies described in Table 1, at the start of vaccination, cats ranged in age from 4 to 10 months. Two to three doses of vaccine were delivered in the time interval described. Control immunizations included the Norden LEUKOCELL vaccine or adjuvant only. Cats were challenged with either F6A virus from AH927-61E ($10^5$–$10^6$ ffu administered intraperitoneally) or FeLV CSU field isolate virus #05821 ($10^5$ ffu delivered intranasally). The challenge was or was not accompanied by treatment of the cats with corticosteroids as noted in Table 1. Cats were bled from the jugular vein post challenge and assessed for FeLV viremia by p27 ELISA antigen detection in the serum and by immunofluorescence in blood cells. Cats with persistent viremia are considered to have been successfully infected by the challenge. Cats resisting persistent viremia are considered uninfected, i.e., to have resisted challenge. When cats are immunosuppressed, 75%–83% of control animals develop persistent viremia after challenge. Without immunosuppression, 60% of animals develop viremia. In subsequent studies, doses of challenge virus have been increased in order to produce 100% viremia in control animals. Only 5% of all 61E immunized animals developed persistent viremia. In one study (CSUJJ4), 100% of 61E cats resisted viremia from challenge with a heterologous FeLV isolate (05821) of the AB subtype, while only 25% of control cats resisted the challenge. This confirms the ability of the 61E-based vaccine preparation to protect against a heterologous challenge such as would occur in nature. In study CSUFD1, only two inoculations were adequate to protect 100% of animals from viremia (60% of control animals viremic).

TABLE 1

| Vaccine designation | Experiment designation | Vaccine administered on weeks | Total no. doses | Challenge on week no. | Challenge virus | Corticosteroid challenge enhancement used on weeks | Age of cats at start of vaccination (months) | No. cats with persistent viremia[a]/ no. cats challenged | Percent of cats which developed persistent viremia (progressors) | Mean percent viremic | Percent of cats which resisted viremia (regressors) | Mean percent resistance |
|---|---|---|---|---|---|---|---|---|---|---|---|---|
| FeLV-61E | CSU1 | 0, 2, 4 | 3 | 6 | 05821 | 0, 1 | 6–8 | 1/6 | 16 | 5 | 84 | 9.5 |
|  | CSUJJ4 | 0, 2, 14 | 3 | 18 | 05821 | 0, 1 | 8–9 | 0/4 | 0 |  | 100 |  |
|  | CSUFD1 | 0, 3 | 2 | 4 | 61E | none | 7–8 | 0/10 | 0 |  | 100 |  |
|  |  |  |  |  |  |  |  | 1/20 |  |  |  |  |
| Norden Leukocell ™ | CSU1 | 0, 2, 4 | 3 | 16 | 05821 | 0, 1 | 4–5 | 6/6 | 100 | 72.2 | 0 | 27.8 |
|  | CSUJJ4 | 0, 2, 14 | 3 | 18 | 05821 | 0, 1 | 9–10 | 1/4 | 25 |  | 75 |  |
|  | CSUJJ2 | 0, 2, 10 | 3 | 21 | 05821 | 0, 1 | 6–7 | 3/4 | 75 |  | 25 |  |
|  | CSUJJ1 | 0, 3, 7, 12 | 4 | 13 | 05821 | 0, 1 | 6–8 | 3/4 | 75 |  | 25 |  |
|  |  |  |  |  |  |  |  | 13/18 |  |  |  |  |
| Adjuvant controls | CSUJJ4 | 0, 2, 14 | 3 | 18 | 05821 | 0, 1 | 6–8 | 3/4 | 75 | 73.6 | 25 | 26.4 |
|  | CSUJJ3 | 0, 2, 10 | 3 | 16 | 05821 | 0, 1 | 6–7 | 3/4 | 75 |  | 25 |  |
|  | CSU1 | 0, 2, 4 | 3 | 6 | 05821 | 0, 1 | 8–9 | 5/6 | 83 |  | 17 |  |
|  | CSUFD1 | 0, 2 | 2 | 4 | 61E | none | 7–8 | 3/5 | 60 |  | 40 |  |
|  |  |  |  |  |  |  |  | 14/19 |  |  |  |  |

[a] Consistently positive for FeLV gag (p27) antigen in plasma by ELISA and in blood cells by immunofluorescence.

Example IV

Generation of FeLV-Induced Disease Model

Figure 4B:
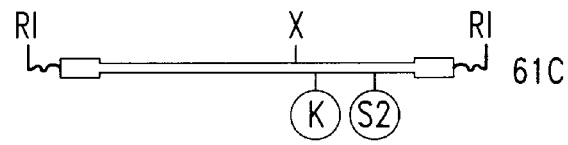

In the intestinal DNA preparation from which molecular clone 61E was isolated, an equal copy number of variant genomes (as defined by restriction enzyme polymorphism; see FIG. 2) was noted. A molecular clone corresponding to a prototype of the "variant A" genome referred to as 61C was isolated in a bacteriophage vector and subsequently inserted in a plasmid vector (FIG. 4b). The plasmid was used to transfect feline fibroblast and T-lymphocyte cultures in vitro. The sequence failed to encode infectious virus. When cotransfected with pFeLV-61E, FeLV-61C was highly infectious and the resulting mixture was cytopathic for T-lymphocytes.

Figure 4C:
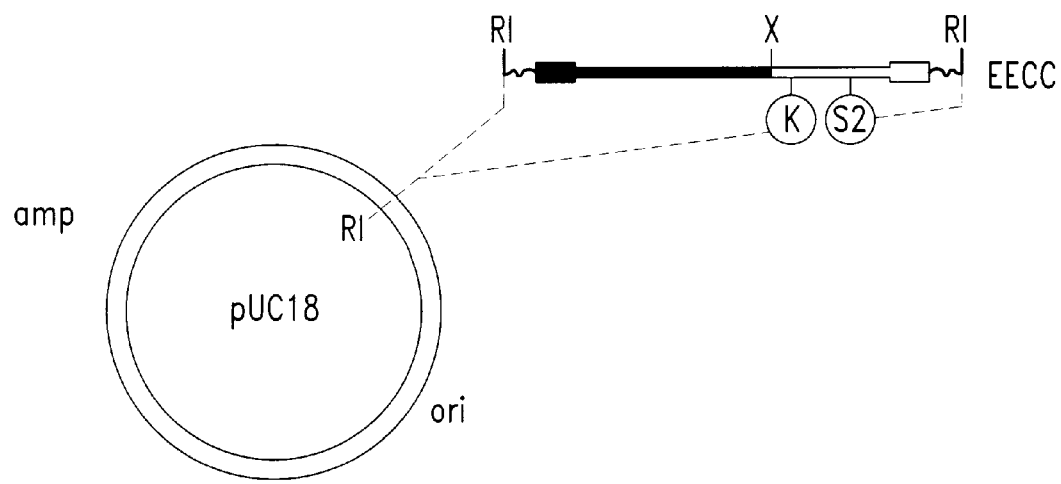

A chimeric virus was constructed in vitro between pFeLV-61E and pFeLV-61C, exchanging sequences on either side of the unique Xho I restriction site found in each provirus at approximately nucleotide position 5817. The 5' terminal sequences were derived from pFeLV-61E, and the 3' sequences were derived from FeLV-61C. The plasmid referred to as pFeLV-EECC (FIG. 4c) was used to transfect feline T-lymphocyte cultures in vitro and shown to encode infectious cytopathic virus.

Both the FeLV-61E/61C virus mixture and FeLV-EECC have been shown to induce fatal immunodeficiency disease (Hoover, *Blood* 70:1880–1892, 1987; Overbaugh, *Science* 239:906–910, 1988) in all inoculated and persistently viremic cats. The replication-competent FeLV-EECC and similar chimeras induce shorter latency disease, with survival times ranging from 20 to 60 days following inoculation of weanling cats. Survival times for animals inoculated with the FeLV-61E/61C mixture range from 90–120 days.

The nucleotide sequence of the portion of the 61C genome found in the FeLV-EECC chimera was determined and the divergent sequences relative to FeLV-61E identified (FIG. 3). The mixture and chimera are the first fully defined retroviruses shown to induce fatal immunodeficiency disease in any organism. They may therefore be used for identification of genetic sequences responsible for AIDS induction in cats, evaluation of anti-viral drug efficacy, as challenge viruses for evaluation of the efficacy of vaccines in preventing viremia and disease, and in the development of vaccines to stimulate immunity against feline leukemia viruses.

Although the foregoing invention has been described in some detail by way of illustration and example for purposes of clarity of understanding, it will be obvious that certain changes and modifications may be practiced within the scope of the appended claims.

We claim:

1. A method of producing a FeLV vaccine, comprising:
   transfecting a mammalian host cell with a recombinant plasmid capable of directing the expression of the proviral genome of a FeLV-A subtype, said plasmid comprising a DNA sequence encoding the proviral genome of a FeLV-A subtype;
   growing said host cell in an appropriate medium;
   harvesting the FeLV-A subtype; and
   inactivating the FeLV-A subtype.

2. The method of claim 1 including, after the step of inactivating, concentrating the FeLV-A subtype to achieve an antigenic mass.

3. The method of claim 1 wherein the step of inactivating comprises exposing the FeLV-A subtype to formalin, beta-propriolactone or binary ethyleneimine under conditions and for a time sufficient to inactivate the FeLV-A subtype.

4. The method of claim 1 wherein the DNA sequence is derived from a clone selected from the group consisting of clones 61E, EECC and naturally occurring variants of Clones 61E or EECC.

5. A method of producing a FeLV vaccine, comprising:
   cotransfecting a mammalian host cell with a recombinant plasmid capable of directing the expression of the proviral genome of a FeLV-A subtype, said plasmid comprising a DNA sequence derived from the clone 61C or a naturally occurring variant thereof, and a DNA sequence derived from a FeLV-A clone which is replication competent;
   growing said host cell in an appropriate medium;
   harvesting the FeLV-A subtype; and
   inactivating the FeLV-A subtype.

6. The method of claim 5 wherein the FeLV clone which is replication competent is clone 61E or a naturally occurring variant thereof.

7. The method of claim 5 including, after the step of inactivating, concentrating the FeLV-A subtype to achieve an antigenic mass.

8. A method of producing a FeLV vaccine, comprising:
   infecting a mammalian host cell with a replication competent virus of the FeLV-A subtype;
   growing said host cell in an appropriate medium;
   harvesting the FeLV-A subtype; and
   inactivating the FeLV-A subtype.

9. The method of claim 8 wherein the FeLV-A subtype is encoded by clone 61E, clone EECC or a naturally occurring variant of Clone 61E or Clone EECC.

10. The method of claim 8 wherein the FeLV-A subtype is encoded by a DNA sequence derived from clone 61E or a naturally occurring variant thereof, in combination with a DNA sequence derived from clone 61C or a naturally occurring variant thereof.

11. A method for protecting a feline host from FeLV infection, comprising:
    administering to a feline host an immunogenically effective amount of a composition comprising an inactivated FeLV-A subtype in combination with a physiologically acceptable carrier or diluent.

12. The method of claim 11 wherein the carrier or diluent is selected from the group consisting of sterile water and phosphate-buffered saline.

13. The method of claim 11 wherein the composition includes a suitable adjuvant.

14. The method of claim 13 wherein the adjuvant is selected from the group consisting of RIBI adjuvant, oil adjuvants, particulate adjuvants and general immune stimulating adjuvants.

15. The method of claim 13 wherein the adjuvant is Freund's adjuvant or incomplete Freund's adjuvant.

16. The method of claim 11 wherein the physiologically acceptable carrier or diluent comprises cell-free supernatant derived from FeLV-A subtype-producing cells.

17. The method of claim 16 wherein the physiologically acceptable carrier or diluent further includes whole cell lysates of FeLV-A subtype-producing cells.

18. The method of claim 11 wherein the composition includes approximately $1-5\times10^5$ focus-forming units of inactivated FeLV-A subtype per kilogram of feline host weight.

19. The method of claim 11 wherein the composition is administered subcutaneously, intramuscularly, intraperitoneally or intravenously.

20. A vaccine against FeLV-induced disease, comprising an inactivated FeLV-A subtype in combination with a suitable adjuvant.

21. The vaccine of claim 20 wherein the adjuvant is selected from the group consisting of RIBI, oil adjuvants, particulate adjuvants and general immune stimulating adjuvants.

22. The vaccine of claim 20 wherein the adjuvant is Freund's adjuvant or incomplete Freund's adjuvant.

23. The vaccine of claim 20 wherein the FeLV-A subtype is encoded by a DNA sequence derived from clone EECC or a naturally occurring variant thereof.

24. The vaccine of claim 20 wherein the FeLV-A subtype is encoded by a DNA sequence derived from clone 61E or a naturally occurring variant thereof.

25. A vaccine against FeLV-induced disease, comprising a FeLV-A subtype encoded by a DNA sequence derived from clone 61E or a naturally occurring variant thereof, in combination with a FeLV-A subtype encoded by a DNA sequence derived from clone 61C or a naturally occurring variant thereof, and a physiologically acceptable carrier or diluent.

* * * * *

UNITED STATES PATENT AND TRADEMARK OFFICE
CERTIFICATE OF CORRECTION

PATENT NO. : 6,042,835   Page 1 of 1
APPLICATION NO. : 08/233004
DATED : March 28, 2000
INVENTOR(S) : Edward A. Hoover et al.

It is certified that error appears in the above-identified patent and that said Letters Patent is hereby corrected as shown below:

Column 1
Line 11, insert --STATEMENT OF GOVERNMENT INTEREST This invention was made with government support under CA001058 and CA043216 awarded by the National Institutes of Health. The government has certain rights in the invention--.

Signed and Sealed this

Twenty-second Day of June, 2010

David J. Kappos
*Director of the United States Patent and Trademark Office*